United States Patent [19]

Elster et al.

[11] 4,161,604
[45] Jul. 17, 1979

[54] PROCESS FOR MAKING 1-HYDROXYETHYL-2-UNDECYL-2-IMIDAZOLINE

[75] Inventors: Charles H. Elster, River Vale, N.J.; Gabriel J. Gibs, Pearl River, N.Y.

[73] Assignee: Lonza Inc., Bergen, N.J.

[21] Appl. No.: 868,350

[22] Filed: Jan. 10, 1978

[51] Int. Cl.$^2$ ........................................... C07D 233/64
[52] U.S. Cl. ..................................... 548/352; 548/347
[58] Field of Search ................................ 548/352, 347

[56] References Cited

U.S. PATENT DOCUMENTS

| 2,528,378 | 10/1950 | Mannheimer | 548/354 |
| 2,528,379 | 10/1950 | Mannheimer | 548/352 |
| 2,892,812 | 6/1959 | Helbing | 560/94 |
| 3,408,361 | 10/1968 | Mannheimer | 548/352 |

FOREIGN PATENT DOCUMENTS

| 904446 | 8/1962 | United Kingdom | 560/94 |
| 950535 | 2/1964 | United Kingdom | 560/94 |

Primary Examiner—Richard Raymond
Attorney, Agent, or Firm—Bert J. Lewen

[57] ABSTRACT

A method for producing 1-hydroxyethyl-2-undecyl-2-imidazoline is disclosed. Lauric acid is reacted with a molar excess of aminoethylethanolamine (AEEA) under vacuum. A first column containing vapor-liquid contact means is used to rectify the reactor overhead vapor (water of reaction plus AEEA); the overhead (water) is discarded; and the bottoms (primarily AEEA) returned directly to the reactor. After substantially all the water has been removed, the reactor overhead is fed to a second column, which is devoid of vapor-liquid contact means, whereby unreacted AEEA is removed. A high purity product remains in the reactor. Other carboxylic acids, such as, fatty acids, may be used in place of lauric acid, and other diamines, such as, ethylenediamine and diethylenetriamine, may be used in place of AEEA, to produce the analogous imidazolines.

12 Claims, No Drawings

PROCESS FOR MAKING 1-HYDROXYETHYL-2-UNDECYL-2-IMIDAZOLINE

BACKGROUND OF THE INVENTION

This invention relates to an improved process for producing high purity 1-hydroxyethyl-2-undecyl-2-imidazoline, which is an intermediate in the manufacture of surfactants.

In the prior art, it was well known that 1-hydroxyethyl-2-undecyl-2-imidazoline could be prepared by the reaction of lauric acid and aminoethylethanolamine. For example, in U.S. Pat. No. 2,528,378 (the '378 patent) equimolar amounts of lauric acid and aminoethylethanolamine (AEEA) were reacted in the liquid phase and the water of reaction was distilled off to drive the reaction to completion.

That process, however, was not satisfactory because unwanted diamides were formed which precipitated and grained out from solutions at room temperature. This made the final products manufactured from the imidazoline unacceptable for use in commercial products, such as, cosmetics.

In order to overcome this problem, it was proposed in U.S. Pat. No. 3,408,361 (the '361 patent) that the reaction be performed using a large excess of the diamine with the addition, during the process, of additional amounts of the diamine well below the surface of the reaction mass. In the '361 patent, this addition was considered mandatory because in the process described, the diamine was lost overhead along with the water of reaction. The amount of amine added each period was "at least equal to the amount . . . which [would] be distilled out before the next addition [was] made" (column 5, lines 40 to 44). This procedure, while reducing the diamide formation, proved cumbersome and unnecessarily complicated the process for forming the desired product.

In order to overcome the foregoing drawbacks, applicants have discovered that 1-hydroxyethyl-2-undecyl-2-imidazoline may be prepared by a straightforward process giving products of high purity. This is accomplished by initially charging the fatty acid to the reaction zone along with a molar excess of the diamine. By using a first distillation zone having vapor-liquid contact area, the water may be removed overhead without the loss from the system of more than trace amounts of the diamine. Subsequently, when the reaction is substantially complete, the vapor from the reaction zone is fed to a second distillation zone whereby at least some, and usually most, of the remaining unreacted AEEA may be removed. This second zone is substantially devoid of any vapor-liquid contact area. The product remaining in the reaction zone after the excess diamine is removed is of high purity.

SUMMARY OF THE INVENTION

In the present invention, lauric acid and AEEA (at least a 5% and usually a 20% molar excess) are reacted under vacuum to form 1-hydroxyethyl-2-undecyl-2-imidazoline. In contrast to the process of the '361 patent in which the AEEA-water vapor from the reactor is condensed and removed from the system, the AEEA-water vapor in the instant process is fed directly to a first (rectification) column from which separated AEEA flows from the column bottom directly back into the reactor. The water of reaction is discarded after optional processing to remove impurities.

After the reaction is substantially complete (as shown by removal of approximately the stoichiometric amount of water), excess AEEA is removed from the product in the reactor. Conventionally, one would expect to be able to continue to use the first column to take the AEEA overhead. However, it has been found that by employing a second column substantially devoid of vapor-liquid contact means for this purpose instead of the first column, which contains such means, much of the excess AEEA may be recovered overhead without raising the reactor temperature and degrading the product quality.

In contrast to the process of the '361 patent, batch additions of fresh AEEA need not be made, the AEEA inventory per batch is greatly reduced, control of the system is simplified, the AEEA need not be fed into a vacuum system, the water by-product recovered is substantially free from AEEA, the excess AEEA is recovered separately for reuse in the next production cycle, high purity imidazoline is produced, and thermal degradation of the imidazoline is prevented.

Other carboxylic acids, such as, fatty acids, may be employed instead of lauric acid, and other diamines, such as, ethylenediamine and diethylenetriamine, may be employed instead of AEEA to produce the analogous imidazolines.

DESCRIPTION OF THE INVENTION 1-hydroxyethyl-2-undecyl-2-imidazoline (IV) is produced according to the following two-step reaction:

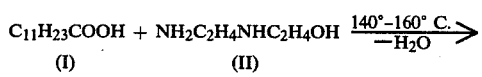
(I)    (II)

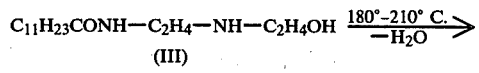
(III)

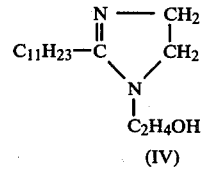
(IV)

In the first step, lauric acid (I) and aminoethylethanolamine (II) react to form an amide (III) and one mole of water. This reaction occurs between 140°–160° C. As the temperature is raised to above 180° C., the amide cyclizes to imidazoline and another mole of water splits off. A molar excess of AEEA must be present throughout the reaction (usually at least 5% molar excess) to reduce the formation of undesirable amidoester and diamide and to catalyze the cyclization.

In a typical processing procedure according to the present invention, a tank-type reactor is employed, preferably equipped with heating, cooling, and agitation means. The AEEA is placed in the reactor and agitation commenced. The lauric acid is then added and the temperature raised to speed dissolution. After this, the system is brought under vacuum (usually less than 100 mm Hg absolute and preferably approximately 50 mm Hg absolute), and the temperature is raised to about 140° C. to initiate the reaction.

During the reaction period, the reactor vapor (AEEA and water) is fed continuously to a first column and the liquid bottoms from the column (essentially all AEEA) flows back into the reactor. By placing the column above the reactor, the column bottoms can continuously flow directly from the column to the reactor by gravity. The thus internally recycled AEEA falls through the reactor vapor space to mix with the liquid reaction mass.

The first column is equipped with a condenser to provide column reflux and contains vapor-liquid contact means, such as, trays, plates, or packing. Preferably packing is used. The vacuum-producing means, e.g., ejector or vacuum pump, is connected to the associated reflux drum.

It is desirable that there be at least some small amount of internal reflux in the column, corresponding to an L/V at the top stage of at least 0.001/1. Reflux corresponding to low internal reflux ratios can be provided by condensation inside the column due to heat loss.

If higher internal reflux ratios are employed, external reflux usually must be provided unless the column's heat loss is allowed to increase. An external reflux ratio of about 3/1 (an internal reflux ratio of about ¾) when using four feet of one inch Pall Ring packing has been found satisfactory. Generally, the external reflux ratio will not exceed 50/1, usually not more than 20/1, and preferably not more than 10/1. Naturally as the number of theoretical contact stages increases, the required reflux ratio will decrease.

As will be understood by those skilled in the art, "internal reflux ratio" is the ratio of (a) liquid fed to a distillation stage (e.g., a tray) to (b) the vapor leaving that stage. The ratio is usually referred to as "L/V," usually in units of moles of liquid per mole of vapor. "External reflux ratio" is the ratio of (a) condensed column overhead product recycled (refluxed) to the column from its associated condenser and reflux drum to (b) product not refluxed, i.e., distillate. The ratio is usually referred to as "L/D," in units of moles of liquid per mole of distillate.

Over a period of two hours, the reactor is heated from 140° to 180° C., after which the external reflux ratio may be reduced, provided there is sufficient internal reflux for water-AEEA separation. The temperature slowly is increased to 208° C. during the next three hours. This temperature is maintained for one and one-half hours to complete the reaction and removal of water.

The reactor vapor overhead, which has become substantially water-free, is then fed to a second column, which is free of vapor-liquid contact means, to remove the excess AEEA. The only reflux in the second column is the small incidental amount of vapor condensing inside the system. The pressure in the reactor is reduced to 23 mm Hg absolute and stripping of the AEEA continues for one hour.

When stripping is finished, the reactor is cooled for at least eight hours. To minimize loss of product color during cooling, agitation is halted, the batch is blanketed with nitrogen, and pressure increased slowly to atmospheric.

The batch is then analyzed for imidazoline content. If it is too low (e.g., less than 90%) additional AEEA is generally added, depending on how much AEEA remains after stripping, and the batch is reheated and reacted under vacuum until the desired value is reached. Often, some AEEA is allowed to remain in the product but usually not more than 3%.

Other monocarboxylic acids may advantageously be employed herein instead of lauric acid, with similar results. These other acids may be saturated or unsaturated, synthetic or naturally occurring (of animal or vegetable origin), and include long-chain fatty acids from coconut, palm, soybean, linseed, cottonseed, rapeseed, olive, peanut, and caster oil. The carboxylic acids may also contain aryl groups or be naphthenic. Mixtures of acids may be used.

The acids employed herein have the general formula $R^1COOH$, where $R^1$ is a hydrocarbyl radical having 3 to 40 carbon atoms. Usually $R^1$ is an alkyl group containing from 5 to 21 carbon atoms. Preferably $R^1$ is alkyl having from 7 to 17 carbon atoms, and, most preferably, the acid is lauryl acid ($R^1$ is $C_{11}H_{23}$—).

Other diamines may be used in place of the AEEA, such as, ethylenediamine and diethylenetriamine. The diamines used herein have the general formula $NH_2CH_2CH_2NHR^2$, where $R^2$ is hydrogen or a branched or straight-chain optionally-substituted alkyl or alkaryl group having from 1 to 15 carbon atoms, preferably 2 to 10 carbon atoms. Any substitution group may be used so long as it does not adversely affect the production of the imidazoline. Examples of substitution groups which may be used include nitro, amino, hydroxy, sulfur-containing, cyano, and halo. More than one such group may be present. Most preferably $R^2$ is —H, —$CH_2CH_2NH_2$, or —$CH_2CH_2OH$.

The imidazolines produced by the present process have the following general formula

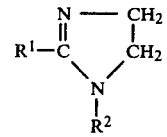

where $R^1$ and $R^2$ have the meanings given above.

The reaction temperature, pressure, and time vary depending on which acids and diamines are employed. The minimum temperature which can be used in each case is the reaction initiation temperature and the maximum temperature is just below the product degradation temperature. Generally, the temperature during a reaction cycle will range from 50° to 300° C., usually from 120° to 240° C., and preferably from 140° to 210° C.

As will be understood by one skilled in the art, the pressure employed must be low enough so that the desired processing temperatures can be achieved. The pressure over the cycle is generally below 300 mm Hg absolute, usually below 200 mm Hg absolute, and preferably below 100 mm Hg absolute.

The duration of the cycle varies with the reactants, temperature, and pressure employed. Generally, the reaction to form the imidazoline takes from 2 to 20 hours, usually from 5 to 10 hours, preferably from 6 to 7 hours. Stripping the unreacted diamine takes from 1 to 10 hours, usually from 1 to 4 hours, preferably from 1 to 2 hours.

Usually at least a 5% molar excess of the diamine is employed, although in some cases a 20% excess is used. Preferably, not more than a 50% molar excess is used.

The following example is provided for illustrative purposes only and should not be construed to limit the scope of the claims.

EXAMPLE

A one-liter three-neck flask equipped with thermometer, vacuum gauge, and stirrer is used. Lauric acid (400 grams or 2 g-moles) and AEEA (249.7 grams of 2.4 g-moles, 20% above theoretical) are reacted in accordance with the above specific procedure for this reaction. The first column is ¾" diameter×21" long and is packed with ¼"×¼" Raschig Rings. The second column is ¾" diameter×3" long. The two columns are arranged in parallel and vapor feed from the reactor may be switched from one to the other by means of a valve. No external reflux is supplied to the first column.

Analysis of the water distillate from the first column indicates that the loss of AEEA during the water-removal step, i.e., before the AEEA stripping step using the second column, is less than 0.7% of the total AEEA employed. The amount of imidazoline produced is 515 g (1.91 g-moles), i.e., 96% of theory. Following AEEA stripping, an imidazoline product of 93+% purity is obtained.

It will be apparent to one skilled in the art that variations and modifications may be made in the above process without departing from the essence of the invention, and the following claims are intended to cover all such variations and modifications.

We claim:

1. A process for producing a high purity imidazoline comprising the following steps:
    (a) reacting a carboxylic acid and at least a 5% molar excess of a diamine in the liquid phase in a reactor under vacuum, thereby forming the imidazoline and water of reaction vapor;
    (b) passing at least some of the vaporized water into a first distillation zone having vapor-liquid contact means;
    (c) removing water substantially free of the diamine as the distillate from the first distillation zone;
    (d) continuing steps (a), (b), and (c) until substantially all of the water of reaction formed has been removed;
    (e) thereafter vaporizing and feeding the unreacted diamine into a second distillation zone substantially devoid of any vapor-liquid contact means, thereby obtaining a high purity imidazoline product as the residue in said reaction zone;
    said carboxylic acid having a formula of $R^1COOH$ where $R^1$ is a hydrocarbyl radical of from 3 to 40 carbon atoms and said diamine having a formula of $NH_2CH_2CH_2NHR^2$ where $R^2$ is hydrogen or an optionally-substituted alkyl or alkaryl group having from 1 to 15 carbon atoms.

2. The process of claim 1 wherein the temperature is from 50° to 300° C.

3. The process of claim 1 wherein the pressure is less than 300 mm Hg absolute.

4. The process of claim 1 wherein $R^1$ is an alkyl group having from 5 to 21 carbon atoms.

5. The process of claim 1 where $R^2$ contains from 2 to 10 carbon atoms.

6. The process of claim 1 wherein the temperature is from 120° to 240° C. and the pressure is less than 200 mm Hg absolute.

7. The process of claim 6 wherein $R^1$ is an alkyl group having from 7 to 17 carbon atoms.

8. The process of claim 6 wherein $R^2$ is —H, —$CH_2CH_2NH_2$, or —$CH_2CH_2OH$.

9. A process for producing high purity 1-hydroxyethyl-2-undecyl-2-imidazoline comprising the following steps:
    (a) reacting lauric acid and at least a 5% molar excess of aminoethylethanolamine in the liquid phase in a reactor, thereby forming the imidazoline and water of reaction vapor;
    (b) passing at least some of the vaporized water into a first distillation zone having vapor-liquid contact means;
    (c) removing water substantially free of aminoethylethanolamine as the distillate from the first distillation zone;
    (d) continuing steps (a), (b), and (c) until substantially all of the water of reaction formed has been removed;
    (e) thereafter vaporizing and feeding the unreacted aminoethylethanolamine into a second distillation zone substantially devoid of any vapor-liquid contact means, thereby obtaining a high purity 1-hydroxyethyl-2-undecyl-2-imidazoline product as the residue in said reaction zone.

10. The process of claim 9 wherein the temperature is from about 140° to about 208° C.

11. The process of claim 9 wherein the pressure is less than 100 mm Hg absolute.

12. The process of claim 9 wherein at least a 20% molar excess of aminoethylethanolamine is employed in step (a).

* * * * *